United States Patent
Manabe et al.

(10) Patent No.: US 11,179,429 B2
(45) Date of Patent: Nov. 23, 2021

(54) HOP OXIDATION-REACTION PRODUCT, PREPARING METHOD THEREOF AND USE THEREOF

(75) Inventors: Fumitoshi Manabe, Yokohama (JP); Yoshimasa Taniguchi, Yokohama (JP); Yumie Kobayashi, Yokohama (JP); Mikio Katayama, Yokohama (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 468 days.

(21) Appl. No.: 13/994,624

(22) PCT Filed: Dec. 15, 2011

(86) PCT No.: PCT/JP2011/079084
§ 371 (c)(1),
(2), (4) Date: Aug. 7, 2013

(87) PCT Pub. No.: WO2012/081675
PCT Pub. Date: Jun. 21, 2012

(65) Prior Publication Data
US 2013/0316023 A1 Nov. 28, 2013

(30) Foreign Application Priority Data

Dec. 15, 2010 (JP) .............................. JP2010-279931

(51) Int. Cl.
*A61K 36/185* (2006.01)
*A23L 33/105* (2016.01)

(52) U.S. Cl.
CPC .......... *A61K 36/185* (2013.01); *A23L 33/105* (2016.08); *A23V 2002/00* (2013.01)

(58) Field of Classification Search
CPC .................................................. A61K 36/185
USPC ........................................................ 424/770
See application file for complete search history.

(56) References Cited

U.S. PATENT DOCUMENTS

2004/0161491 A1* 8/2004 Ting .................... C12C 3/08
426/11
2006/0083775 A1 4/2006 Rigby et al.

FOREIGN PATENT DOCUMENTS

| EP | 2441463 A1 | 4/2012 |
| JP | 2008-212041 A | 9/2008 |
| JP | 2008212041 A * | 9/2008 |
| WO | WO 2003/068205 A1 | 2/2003 |
| WO | WO 2010/143719 A1 | 12/2010 |

OTHER PUBLICATIONS

International Preliminary Report on Patentability in PCT/JP2011/079084 dated Jun. 27, 2013.
Supplementary European Search Report dated Sep. 29, 2014, in EP 11849798.1.
Hertel et al., "Possibilities for increasing bitter compound yields in beer brewing. Part 2," Brauwelt, Nuernberg DE, Jan. 1, 2009, 149(14):394-398.
Database WPI Week 201017, Thomson Scientific, London, GB, AN 2010-C05359, XP002729707 & JP 2010 043064 A (Sapporo Breweries Ltd) Feb. 29, 2010, abstract.
Hertel, Marcus et al.. Trageted isomerization: studies in increasing hop yield, Brauindustrie, Oct. 2010, 95 (10), pp. 38-40, (abstract) [online] STN, CAPLUS, AN.2010:1347325, DN. 154:257717.
Lyashenko N I,"Study of Bitter Substance Eontent in Hop Lupulin and Their Effective Use", Prikladnaya Biokhimiya I Mikrobiologiya, 1978, vol. 14, No. 1, pp. 144-149, (abstract) [online] STN, BIOSIS, AN. 1978:233125, DN.PREV197866045622.
PCT/JP2011/079084 international Search Report, completion date Mar. 13, 2012.
Office Action dated Aug. 25, 2015, in JP 2012-548835, with English translation.
Decision of Rejection dated Jan. 29, 2016, in JP 2012-548835, with English translation.
Office Action dated Feb. 1, 2016, in EP 11849798.1.
European Search Report dated Oct. 13, 2017, in EP 17183259.5.

* cited by examiner

*Primary Examiner* — Michael Barker
(74) *Attorney, Agent, or Firm* — Foley & Lardner LLP (57) ABSTRACT

The present invention relates to a food product and food additive comprising a hop oxidation-reaction product or an extract thereof, as well as to a fat accumulation suppressing agent and a weight gain suppressing agent having it as an active ingredient.

14 Claims, 6 Drawing Sheets

Drawings
[Fig. 1A]

| Heating temperature | Heating time | IC50 ($\mu$g/ml) |
|---|---|---|
| 60°C | 32hr | 38.1 |
| 60°C | 48hr | 37.9 |
| 60°C | 120hr | 133.3 |

HOP OXIDATION-REACTION PRODUCT, PREPARING METHOD THEREOF AND USE THEREOF

CROSS-REFERENCE TO RELATED APPLICATIONS

This application is a National Phase of International Application PCT/JP2011/079084, filed Dec. 15, 2011, which was published on Jun. 21, 2012, as WO 2012/081675, which claims the benefit of JP Application No. 2010-279931, filed Dec. 15, 2010, all of which are incorporated herein by reference in their entirety.

TECHNICAL FIELD

The present invention relates to a hop oxidation-reaction product, a preparing method thereof and use thereof. More specifically, the present invention relates to a food product and food additives in which a hop oxidation-reaction product or an extract thereof is used, and to a fat accumulation suppressing agent and a weight gain suppressing agent having a hop oxidation-reaction product or an extract thereof as an active ingredient.

BACKGROUND ART

In recent years, many health conscious foods and drinks are developed, and are even commercially available. In order to obtain a genuine product with which a health function can be acknowledged, obviously, a compounded amount needs to be greater than an effective amount. As in the old saying "Bitters do good to the stomach," a so-called functional component which provides a beneficial effect with the human body often has a bitter taste. If that is the case, food and drink containing a functional component in an amount equal to or more than the effective amount will have decreased palatability, resulting in a less attractive product.

A hop, from which bitter taste components in beer originate, is also used as a folk medicine for many years, and various health functions such as a calming effect and a stomachic property are known. When an extract obtained from the hop is included in food and drink in an amount equal to or more than a certain amount, a characteristic intense bitter taste and harsh taste arise, and may spoil palatability.

Many attempts have been reported in order to remove or suppress such a bitter taste. Substances used as a bitter taste-reducing material include phosphatidic acids (Product name "Benecort BMI" Kao Corp.), L-ornithine (Food Science Journal, Vol. 317, p 54, 2004) and the like. However, none of them necessarily shows a strong effect when used alone, and in particular, the bitter taste of the above hop extract was difficult to be suppressed. Further, in a masking technology (Japanese Patent Laid-Open No. 2008-99682) in which a sweetening agent such as sucralose and thaumatin is added, a bitter taste was masked by sweetness to some extent, but the use thereof is limited due to its strong sweetness.

In the case of pharmaceutical products, sugar coating is mainly used for a tablet in general. In addition, the film coating technology, microencapsulation and the like are also used, but a bitter taste has been difficult to be completely masked. Further, in the case of liquid formulations, such technologies can not be used as in the case of drinks. Therefore, suppression of a bitter taste remains a significant problem in the field of food and drink and pharmaceutical products.

CITATION LIST

Patent Literature

Patent Literature 1: Japanese Patent Laid-Open No. 2008-99682
Patent Literature 2: Japanese Patent No. 4503302

Nonpatent Literature

Nonpatent Literature 1: Food Science Journal, Vol. 317, p 54, 2004

SUMMARY OF INVENTION

Problem to be Solved by the Invention

There is a report that isohumulones, humulones and lupulones from a hop has a PPAR agonist activity, and have a lipid metabolism improving effect via this activity (Japanese Patent No. 4503302). However, since these components from a hop have an intense bitter taste, and suppression of the bitter taste has been an issue when applied to food and drink and pharmaceutical products.

Means for Solving the Problem

The present inventors find that a degradation product obtained by oxidizing a hop has a fat accumulation suppressing effect and a weight gain suppressing effect in spite of significantly reduced contents of humulones and the like therein, and that the degradation product has a significantly reduced bitter taste. The present invention is based on these findings.

Further, according to the present invention, provided is a hop oxidation-reaction product in which the proportion of the peak area of iso $\alpha$ acid, $\alpha$ acid and $\beta$ acid to the total peak area as determined by HPLC analysis is 20% or less.

According to the present invention, also provided are a food additive comprising the hop extract oxidation-reaction product (hereinafter may be called a "the food additive of the present invention") and a food product comprising them (hereinafter may be called "the food product of the present invention").

According to the present invention, further provided is a fat accumulation suppressing agent or a weight gain suppressing agent comprising the hop oxidation-reaction product as an active ingredient(hereinafter, may be simply called "the suppressing agent of the present invention").

According to the present invention, a method of preparing the suppressing agent of the present invention is further provided, the method comprising: oxidizing a hop and optionally extracting an oxidation-reaction product.

According to the present invention, a method of suppressing fat accumulation and a method of suppressing weight gain are further provided, the method comprising: administering the hop oxidation-reaction product to a mammal including human.

According to the present invention, provided is use of the hop oxidation-reaction product in manufacture of a fat accumulation suppressing agent or a weight gain suppressing agent.

The hop oxidation-reaction product of the present invention or an extract thereof has a fat accumulation suppressing effect and/or a weight gain suppressing effect while not having an intense bitter taste as in an isomerized hop. Therefore, the food product of the present invention and the suppressing agent of the present invention are advantageous in that they are expected to show a physiological activity such as fat accumulation suppression and weight gain suppression while they can be ingested as it is without subjecting to a means of masking a bitter taste.

DETAILED DESCRIPTION OF THE INVENTION

HOP Oxidation-Reaction Product

A hop oxidation-reaction product provided by the present invention can be obtained by contacting a hop with oxygen in the air for oxidation. There is no particular limitation for the oxidation treatment in the present invention, but preferably, the oxidation treatment is performed under the conditions of 60° C. to 80° C. and 8 hours to 120 hours. An approach for the oxidation treatment will be described below. Further, any form of a hop can be used in the present invention as long as the hop has a lupulin portion. For example, those before dried after harvest, those dried after harvest, those compressed, those ground and those processed into a pellet can be used. Alternatively, a pellet in which lupulin portions are selectively enriched may be used. Furthermore, a pellet subjected to isomerization may be used.

A hop contains acidic resin components such as α acid (humulones), β acid (lupulones) and iso α acid (isohumulones). The term "humulones" as used in the present invention is meant to include humulone, adhumulone, cohumulone, post-humulone and pre-humulone. Further, the term "lupulones" as used in the present invention is meant to include lupulone, adlupulone, colupulone, post-lupulone and pre-lupulone. Moreover, the term "isohumulones" as used in the present invention is meant to include isohumulone, isoadhumulone, isocohumulone, isoposthumulone, isoprehumulone, Rho-isohumulone, Rho-isoadhumulone, Rho-isocohumulone, Rho-isoposthumulone, Rho-isoprehumulone, tetrahydro isohumulone, tetrahydro isoadhumulone, tetrahydro isocohumulone, tetrahydro isoprehumulone, tetrahydro isoposthumulone, hexahydro isohumulone, hexahydro isoadhumulone, hexahydro isocohumulone, hexahydro isoposthumulone and hexahydro isoprehumulone. Note that isohumulones are present in both cis and trans stereoisomers. Unless otherwise stated, the term is meant to include the both.

According to Examples described below, by subjecting a hop to an oxidation treatment, the contents of α acid, β acid and iso α acid are reduced while the contents of components other than these are increased. Therefore, examples of the "hop oxidation-reaction product" include those in which a proportion of the peak area of α acid, β acid and iso α acid to the HPLC total peak area of the oxidation-reaction product is 20% or less, preferably 10% or less as determined by the HPLC analysis of Example 1.

A component other than α acid, β acid and iso a acid contained in the oxidation-reaction product of the present invention can be easily detected by a well known analytical means such as HPLC. For example, a hop oxidation-reaction product prepared in the procedure described in Example 1 contains compounds other than α acid, β acid and iso α acid, and these compounds (peaks other than α acid, β acid and iso α acid in FIG. 1A) can show a physiological activity as shown in Examples 7 and 8. Therefore, examples of the oxidation-reaction product of the present invention include those in which a proportion of the peak area of a component other than α acid, β acid and iso a acid to the HPLC total peak area of the oxidation-reaction product is 80% or more, preferably 90% or more as determined by the HPLC analysis of Example 1.

It is found that depending on a processing condition or a mode of ingestion, the hop oxidation-reaction product of the present invention may contain fatty acids generated by an oxidation-reaction of humulones, and ingestion may be difficult due to an unpleasant odor as expressed as an oxidized odor or a burning odor.

Therefore, for the oxidation-reaction product of the present invention, an unpleasant odor is preferably removed from the oxidation product. An approach of removing an unpleasant odor will be described below.

The hop oxidation-reaction product of the present invention can be used as an extract obtained by extraction with a solvent containing water or various organic media, and by supercritical extraction using supercritical carbon dioxide and the like. The present invention also includes such embodiments.

Organic solvents include lower alcohols having 1 to 4 carbon atoms such as methanol, ethanol, propanol and butanol; lower alkyl esters such as acetic acid ethyl ester; glycols such as ethylene glycol, butylene glycol, propylene glycol and glycerin; in addition to this, polar solvents such as acetone and acetic acid; hydrocarbons such as benzene and hexane; and non-polar solvents such as ethers such as ethyl ether and petroleum ether. The hop oxidation-reaction product of the present invention in a form of an extract is advantageous in that it can be available in a high concentration, and in addition, has increased storage stability and the like.

Preparation of the Hop Oxidation-Reaction Product Oxidation Treatment

The oxidation-reaction product of the present invention can be manufactured by subjecting a hop to an oxidation treatment.

The oxidation treatment is preferably performed by heating a hop in the air. There no particular limitation for heating temperature, but a preferred upper limit is 100° C., a more preferred upper limit is 80° C.

A heating temperature of 100° C. or below is advantageous for preferential progression of oxidation over isomerization. Further, a lower limit of preferred heating temperature is 60° C. A heating temperature of 60° C. or higher is advantageous for efficient progress of an oxidation-reaction. There is also no particular limitation for a reaction duration, which can be appropriately selected depending on a hop variety and a reaction temperature. For example, 48 to 120 hours are preferred in the case of 60° C., and 8 to 24 hours are preferred in the case of 80° C. Further, there is no particular limitation for a form of a hop as long as it can make a contact with oxygen in the air, but a powdered form is preferred because a reaction time can be shortened. Furthermore, it may be stored under a high humidity environment.

The oxidation treatment can transform $\alpha$ acid, $\beta$ acid and iso $\alpha$ acid contained in a hop to oxides. An extent of oxidation of these components can be analyzed and checked by HPLC and the like.

A hop to be subjected to the oxidation treatment is commercially available as a beer additive, and a commercially available product can be used in the present invention. For example, a pelleted product prepared by compressing hop cone (Type 90 pellet), a pellet in which lupulin portions are selectively enriched (Type 45 pellet) or an isomerized hop pellet (for example, Isomerized Pellets (HopSteiner)).

Treatment for Removing an Unpleasant Odor

An unpleasant odor is associated with an oxidation-reaction product obtained by subjecting a hop to an oxidation treatment. Since the odor may have a negative effect depending on a mode of ingestion, a treatment may be performed in which the unpleasant odor generated by the treatment is removed.

An unpleasant odor can be removed by extracting a hop oxidation-reaction product with an aqueous organic medium. This method is significantly advantageous in that it is very simple and efficient. There is no particular limitation for an aqueous organic medium as long as it is commonly used in food manufacturing, but ethanol is preferred in view of extraction efficiency. There is no particular limitation for extraction temperature, but 60° C. or below is preferred, and 50 to 60° C. is more preferred in view of extraction efficiency. An oxidation-reaction product of an extracted hop can be filtered through a paper filter and the like to remove insoluble components, and then concentrated to give an extract. The extract can be advantageously used in the food additive of the present invention, the food product of the present invention and the suppressing agent of the present invention in a similar way to the hop oxidation-reaction product.

Use of the Hop Oxidation-Reaction Product

As shown in Examples 5 to 6 described below, the oxidation-reaction product of a hop or an extract thereof significantly suppressed the body weight of a high dietary fat intake mouse, and significantly reduced the subcutaneous fat weight of a high dietary fat intake mouse.

Therefore, the oxidation-reaction product of the present invention is useful as a fat accumulation suppressing agent (in particular a subcutaneous fat accumulation suppressing agent) and a weight gain suppressing agent. Further, the oxidation-reaction product of the present invention or an extract thereof is useful for preventing and/or treating obesity.

The oxidation-reaction product of the present invention does not have an intense bitter taste as in humulones and isohumulones (Example 3). Therefore, the degradation product of the present invention is advantageous in that it is expected to have the above physiological activities while it can be used for food and drink or pharmaceutical products as it is without subjecting to a means of masking a bitter taste.

Pharmaceutical Products and Food Products

The oxidation-reaction product of the present invention to be provided as a pharmaceutical product can be manufactured by mixing the degradation product of the present invention with a pharmaceutically acceptable additive. The oxidation-reaction product of the present invention or an extract thereof, which does not have an intense bitter taste as in humulones and isohumulones, has an advantage that it can be formulated without subjecting to a means of masking a bitter taste or in a condition where a bitter taste is fully masked using an existing masking means while it is expected to show a predetermined efficacy.

The oxidation-reaction product of the present invention can be used as an oral or parenteral preparation, but an oral preparation is preferred. Oral preparations include granule, powder, tablet (including sugar coated tablet), pill, capsule, syrups, emulsion and suspension. Parenteral preparations include injectables (for example, subcutaneous injectables, intravenous injectables, intramuscular injectables, intraperitoneal injectables), drops, external preparations (for example, formulation for transnasal administration, transdermal formulation, ointment) and suppository (for example, rectal suppository, vaginal suppository). These formulations can be formulated by an approach commonly performed in the art using a pharmaceutically acceptable carrier. Pharmaceutically acceptable carriers include excipients, binders, diluents, additives, flavoring agents, buffers, thickeners, colorants, stabilizers, emulsifying agents, dispersing agents, suspending agents and antiseptic agents. For example, magnesium carbonate, magnesium stearate, talc, sugar, lactose, pectin, dextrin, starch, gelatin, tragacanth, methylcellulose, sodium carboxymethylcellulose, low melting point wax and cacao butter can be used as a carrier.

For example, a pharmaceutical preparation can be manufactured as described below. An oral preparation can be manufactured by adding an excipient (for example, lactose, white soft sugar, starch, mannitol), a disintegrating agent (for example, calcium carbonate, carboxymethylcellulose calcium), a binder (for example, a pregelatinized starch, gum arabic, carboxymethylcellulose, polyvinylpyrrolidone, hydroxypropylcellulose) or a lubricant (for example, talc, magnesium stearate, polyethylene glycol 6000) to an active ingredient, performing compression molding, and then if desired, performing coating by a publicly acknowledged method for the purposes of masking tastes, enteric-coating, or prolonged duration of effect. For coating agents, the followings can be used: for example ethylcellulose, hydroxymethylcellulose, polyoxyethylene glycol, cellulose acetate phthalate, hydroxypropylmethylcellulose phthalate and EUDRAGIT (Rohm Pharma GmbH, Germany, methacrylic acid-acrylic acid copolymer).

An injectable can be manufactured by dissolving, suspending or emulsifying an active ingredient in an aqueous solvent (for example, distilled water, physiological saline, Ringer's solution and the like) or an oleaginous solvent (for example, vegetable oils such as olive oil, sesame oil, cotton seed oil and corn oil; propylene glycol) or the like along with a dispersing agent (for example, Tween 80 (Atlas Powder Co., U.S.), HCO60 (Nikko Chemicals Co., Ltd.), polyethylene glycol, carboxymethylcellulose, sodium alginate and the like), a preservative (for example, methylparaben, propylparaben, benzyl alcohol, chlorobutanol, phenol), an isotonizing agent (for example, sodium chloride, glycerin, sorbitol, glucose, invert sugar) and the like. In that case, an additive such as a solubilizing agent (for example, sodium salicylate, sodium acetate), a stabilizer (for example, human serum albumin) and a soothing agent (for example, benzalkonium chloride, procaine hydrochloride) may be added if desired.

An external preparation can be manufactured by transforming an active ingredient to a solid, semi-solid, or liquid composition. For example, the solid composition can be manufactured by powdering an active ingredient as it is or powdering an active ingredient to which added and mixed are an excipient (for example, lactose, mannitol, starch, microcrystalline cellulose and white soft sugar), a thickener (for example, natural gums, cellulose derivatives, acrylic acid polymer) and the like. The liquid composition can be manufactured in the almost same way as injectables. The semi-solid composition is preferably an aqueous or oleaginous gel or a cartilage-like substance. Further, each of these compositions may contain a pH regulator (for example, carbonic acid, phosphoric acid, citric acid, hydrochloric acid, sodium hydroxide), a antiseptic agent (for example, parahydroxybenzoate esters, chlorobutanol, benzalkonium chloride) and the like. Suppository can be manufactured by transforming an active ingredient to an oleaginous or aqueous solid, semi-solid, or liquid composition. Oleaginous bases used for the composition include glycerides of higher fatty acids [for example, cacao butter, witepsols (Dynamit Nobel GmbH)], middle fatty acids [for example, migriols (Dynamit Nobel GmbH)] or vegetable oils (for example, sesame oil, soybean oil, cotton seed oil). Aqueous bases include polyethylene glycols and propylene glycol. Further, aqueous gel bases include natural gums, cellulose derivatives, vinyl polymers and acrylic acid polymers.

The food additive of the present invention is the oxidation-reaction product of the present invention intended for addition to a food product. The oxidation-reaction product of the present invention demonstrates a physiological activity such as a fat accumulation suppressing effect, a weight gain suppressing effect and the like as described above. Therefore, the food additives of the present invention also include those intended for addition to a food product to expect a physiological activity of the oxidation-reaction product of the present invention. Targets and modes of addition can be as described for the food product of the present invention.

The food product of the present invention is food and drink containing an effective amount of the oxidation-reaction product of the present invention. The phrase "containing an effective amount" of the oxidation-reaction product of the present invention as used herein means a content in which the hop extract oxidation-reaction product is to be ingested in the range as described below when individual food and drink is consumed in a commonly consumed amount.

In a case where the hop extract oxidation-reaction product of the present invention is provided as a food product, the oxidation-reaction product of the present invention can be included in a food product as it is. More specifically, the food and drink of the present invention can be those in which the hop extract oxidation-reaction product of the present invention is prepared as food and drink as it is; those to which various proteins, saccharides, lipids, trace elements, vitamins and the like are further added; those transformed into a liquid, semi-liquid or solid; those transformed into an aqueous solution of potassium salts, sodium salts and the like; and those added to general food and drink. The oxidation-reaction product of the present invention or an extract thereof, which does not have an intense bitter taste as in humulones and isohumulones, has an advantage that it can be made into a food product without subjecting to a means of masking a bitter taste or in a condition where a bitter taste is fully masked using an existing masking means while it is expected to show a predetermined effect.

Note that in a case where the extract obtained by extracting the oxidation-reaction product of the present invention with an aqueous organic medium is used in a food product, an unpleasant odor as expressed as an oxidized odor or a burning odor advantageously does not arise even when the extract is used in a food product in a high concentration because the unpleasant odor generated from an oxidation-reaction is almost removed.

The term a "food product" as used in the present invention is meant to include health food, functional food, food for specified health use and food for the sick.

Further, a form of the "food product" may not be particularly limited, for example, may be a form of a drink.

The oxidation-reaction product of the present invention can be provided as a food product useful for maintenance and promotion of good health, specifically as the food product also having a function such as a fat accumulation suppressing effect and a weight gain suppressing effect by including the oxidation-reaction product of the present invention in the food for daily ingestion, health food and functional food taken as a supplement, preferably lipid-containing food, high-calorie food and the like because the oxidation-reaction product of the present invention has a fat accumulation suppressing effect and a weight gain suppressing effect. That is, the food product of the present invention can be provided as a food product suitable for consumers who are conscious of fat accumulation (in particular, accumulation of body fat and visceral fat) and consumers who are conscious of weight gain, in particular as food for specified health use.

Specifically, examples of such food and drink include, but not limited to, carbohydrate containing food and drink such as rice food, noodles, bread and pasta; western confectionery such as cookie and cake; Japanese confectionery such as a bun with a bean-jam filling and sweet bean jelly; candy; gum; various confectionaries such as cooled or iced confectionary such as yogurt and pudding; alcoholic beverages such as whiskey, bourbon, spirits, liqueur, wine, fruit wine, sake, Chinese liquor, shochu, beer, non-alcohol beer having 1% or less alcohol content, low-malt beer, other miscellaneous liquors and shochu highball; non-alcoholic beverages such as a drink containing fruit juice, a drink containing vegetable juice, a drink containing fruit juice and vegetable juice, soft drink, milk, soybean milk, milk beverages, drinkable yogurt, drinkable jelly, coffee, cocoa, tea drink, energy drink, sports drink and mineral water; processed products in which eggs are used, processed products of fish (squid, octopus, shellfish, eel and the like) and meat (including giblets such as lever) (including rare delicacy) and the like.

Tea drinks include, for example, black tea, green tea, barley tea, brown rice tea, green tea of middle grade, green tea of highest quality, roasted tea, oolong tea, turmeric tea, puer tea, rooibos tea, rose tea, chrysanthemum tea and herbal tea (for example, mint tea, jasmine tea).

Fruits used for the drink containing fruit juice and the drink containing fruit juice and vegetable juice include, for example, apple, mandarin orange, grape, banana, pear and plum. Further, vegetables used for the drink containing vegetable juice or the drink containing fruit juice and vegetable juice include, for example, tomato, carrot, celery, cucumber and watermelon.

The pharmaceutical product and food and drink of the present invention, which use a hop which human beings have taken as food and drink for many years, show low toxicity, and can be used safely to mammals in need thereof (for example, human, mouse, rat, rabbit, canine, feline, bovine, equine, swine, monkey and the like).

The dosage or intake of the oxidation-reaction product of the present invention can be determined depending on recipient, age and weight of recipient, conditions, administration time, a dosage form, a mode of administration and a combination of medicaments and the like. For example, in a case where the oxidation-reaction product of the present invention is orally administered as a medicine, the oxidation-reaction product is administered 1 to 3 times a day such that the total amount is in the range of 10 to 600 mg, more preferably 20 to 200 mg per day per 60 Kg of adult weight in terms of isohumulone equivalence, and in the case of parenteral administration, the range is 1 to 100 mg, more preferably 3 to 30 mg. The dosage of a drug having a different mechanism of action which is used in combination of the oxidation-reaction product of the present invention can also be suitably determined based on the clinically used dosage for each. Further, in a case where the oxidation-reaction product of the present invention is ingested as a food product, the oxidation-reaction product of the present invention can be included in a food product such that the total amount of the oxidation-reaction product is in the range of 25 to 9600 mg, more preferably 25 to 780 mg per day per 60 Kg of adult weight in terms of isohumulone equivalence.

EXAMPLE

The present invention is specifically described based on the following examples, but the present invention shall not be limited to these examples.

Example 1

Preparation of the Product of Hop Pellet Oxidation-Reaction

For a hop, the pelleted Hallertauer Perle variety (HPE variety) was used. The hop was ground with a mill, and the heating reaction time was kept up to 24 hours at 80° C. The resulting product was pre-treated as described below and then subjected to HPLC analysis.

Pre-Treatment for Product Analysis

A sample of the product was added to ethanol to give 10% w/v, and extracted at 50° C. for 1 hour. The resulting extract was diluted 10 times with ethanol.

HPLC System Configuration

Pump: LC-10Advp×3 (SHIMADZU CORPORATION)

Degasser: DGU-20A5 (SHIMADZU CORPORATION)

System controller: CBM-20A (SHIMADZU CORPORATION)

Autosampler: SIL-20ACHT (SHIMADZU CORPORATION)

Column oven: CTO-20AC (SHIMADZU CORPORATION)

Photodiode array detector: SPD-M 20A (SHIMADZU CORPORATION)

Waveform analysis software: LCSolution (SHIMADZU CORPORATION)

HPLC Conditions

Column: Alltima C18 2.1 mm I.D.×100 mm, particle diameter: 3 µm

Flow rate: 0.6 mL/min

Elution solvent A: water/phosphoric acid, 1000/0.2 (v/v)+ EDTA (free) 0.02% (w/v)

Elution solvent B: acetonitrile

Elution solvent C: water

Injection amount: 3 µL

Column temperature: 40° C.

Detection wavelength: 270 nm (oxidation-reaction products, iso α acid, α acid, β acid)

Gradient Program:

TABLE 1

| Time min | Mobile phase composition % | | |
|---|---|---|---|
| | A | B | C |
| 0 | 90 | 10 | 0 |
| 26.67 | 48 | 52 | 0 |
| 30 | 25 | 75 | 0 |
| 32.67 | 15 | 85 | 0 |
| 37.67 | 15 | 85 | 0 |
| 37.68 | 0 | 10 | 90 |
| 41.3 | 0 | 10 | 90 |
| 41.31 | 90 | 10 | 0 |
| 51 | | stop | |

(After 37.68 min, the washing and equilibration step)

A proportion (%) of the peak area of α acid, β acid and iso α acid to the total area (mAU·min) of all the peaks detected at a detection wavelength of 270 nm under the above analytical conditions was computed. For the waveform analysis, a region in which a solvent peak and a negative peak due to an injection shock occur is excluded from the range of analysis.

Figure 1A:
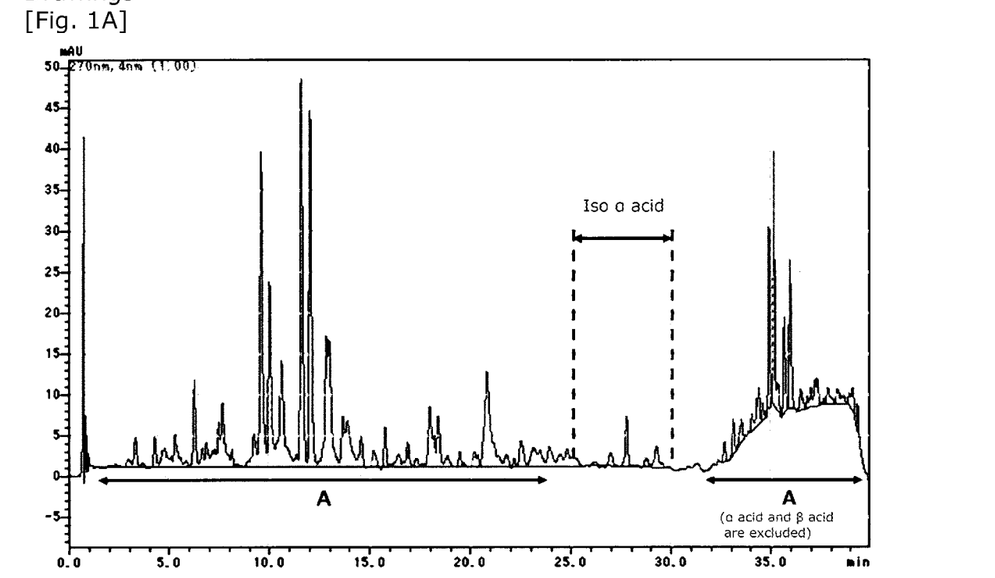
FIG. 1A shows a HPLC chart of a product obtained by oxidizing a hop (Example 1).
Figure 1B:
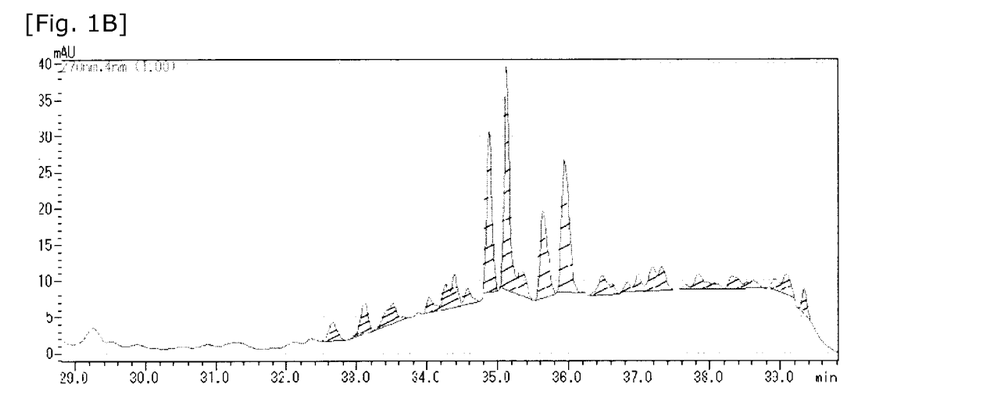
FIG. 1B shows an enlarged view of the HPLC chart of the product obtained by oxidizing a hop (Example 1).

FIG. 1A shows a HPLC chromatogram for the analysis of the product in Example 1. Further, FIG. 1B shows an enlarged view in which the area used for the analysis after 30 minutes are shaded.

Figure 2A:
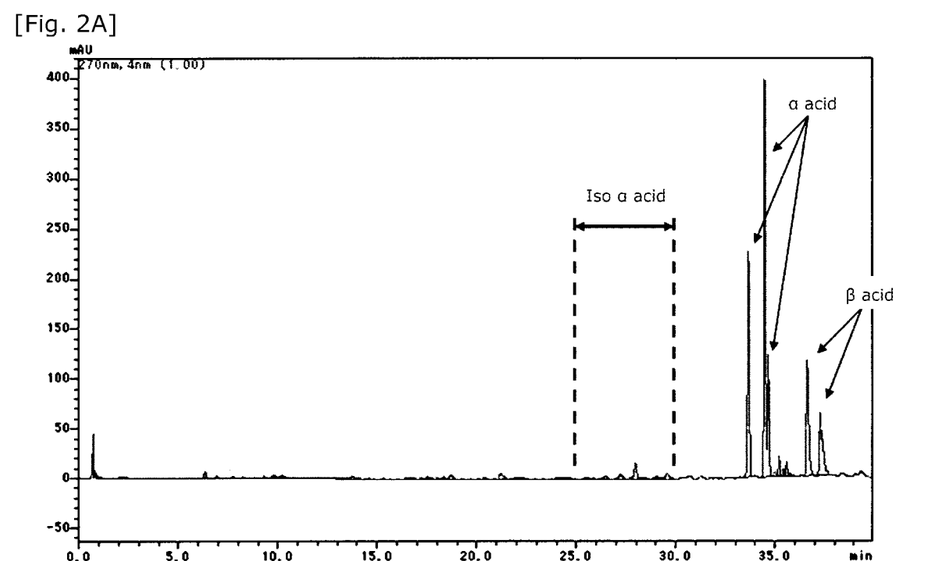
FIG. 2A shows a HPLC chart of a non-oxidized hop.
Figure 2B:
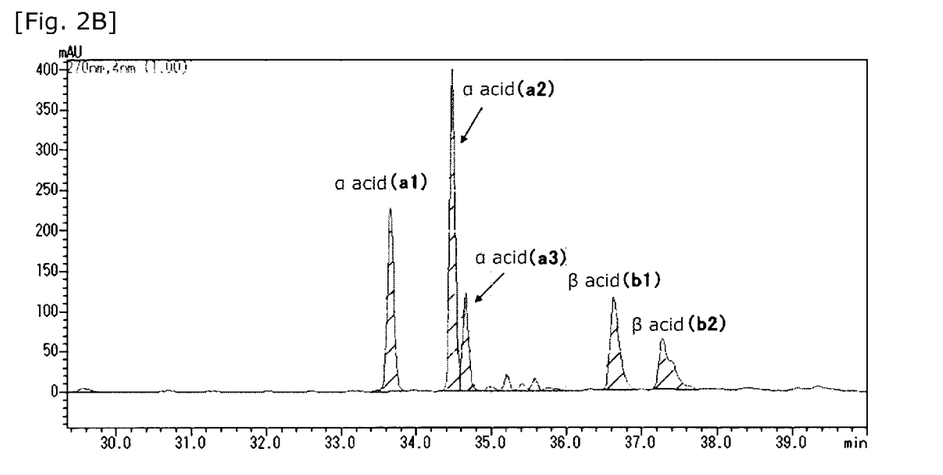
FIG. 2B shows an enlarged view of the HPLC chart of the non-oxidized hop.

FIG. 2A shows a chromatogram for the analysis in which the oxidation treatment was not performed. Further, FIG. 2B showed an enlarged view. With regard to the peaks of α acid and β acid, the retention times of α acid (a1, a2, a3) and β acid (b1, b2) in this analysis are used as reference. a1, a2 and a3 are cohumulone, humulone and adhumulone in this order, and b1 and b2 are colupulone, lupulone and adlupulone, respectively.

The proportion (%) of the peak area of α acid, β acid and iso α acid to the total area (mAU·min) of all the peaks detected at a detection wavelength of 270 nm for each analyzed sample is as shown in Table 2.

TABLE 2

| Reaction conditions | Peak area ratio (%) (α acid, β acid, iso α acid/all peaks) |
|---|---|
| 80° C., 24 hours | 3.0 |
| Untreated | 88.9 |

The results revealed that in the product obtained by the oxidation treatment, the proportion of α acid, β acid and iso α acid to all the peaks was considerably decreased, and α acid, β acid and iso α acid were decreased about 90% as compared with the untreated product.

Further, peaks other than α acid, β acid and iso α acid newly appeared due to the oxidation-reaction. That is, the peaks fractionated in the range indicated by the arrow A (the peaks of α acid and β acid are excluded) in FIG. 1A correspond to these. The proportion (%) of the area of the peaks fractionated in the range indicated by the arrow A (the peaks of α acid and β acid are excluded) to the total area (mAU·min) of all the peaks detected at a detection wavelength of 270 nm was as shown in Table 3.

TABLE 3

| Reaction conditions | Peak area ratio (%) (peaks fractionated in the range indicated by the arrow A) |
|---|---|
| 80° C., 24 hours | 97.0 |
| Untreated | 11.1 |

The quantitative analysis of α acid, β acid and iso α acid contained in the hop or the above product is possible by the above analytical method. As a reference standard for the quantitative analyses of α acid, β acid and iso α acid, for example, Internal Calibration Standards: ICE-2, ICS-I2, ICS-T2 and the like available from American Society of Brewing Chemists (ASBC) can be used.

Example 2

Extraction of the Oxidation-Reaction Product of a Hop (Removal of an Unpleasant Odor)

The product in Example 1 contains fatty acids and the like resulted from the oxidation-reaction, and pleasant ingestion was thought to be difficult because of the unpleasant odor depending on a mode of ingestion. Accordingly, the unpleasant odor was tried to be removed.

Ethanol was added to 100 g of the product of Example 1 to give a volume of 1 L, and stirred at 55° C. for 1 hour to obtain an ethanol extract.

Subsequently, extraction residues were removed by filtration, and 22 g of a dark green solid was obtained by performing concentration.

Sensory evaluation was performed by a panel of six in-house staffs according to the following method for the unpleasant odor of the extract (a dark green solid) from Example 2 prepared by the extraction as described above and the product (a control) from Example 1. The extract of Example 2 or the control was added to a 10 mM citrate buffer solution (approximately pH 5.5), and boiled for 1 hour to dissolve. The solution was filtered, and the evaluation was performed using a solution prepared to contain about 50 ppm of the extract of Example 2 or the control in terms of isohumulone equivalence.

Sensory evaluation was performed in which an odor from a solution was sensed for several seconds, and evaluated in accordance with the evaluation criteria. The result was calculated as the mean of scores form the six staffs, and scored in accordance with the following criteria.

Evaluation Criteria

TABLE 4

| Evaluation items | Evaluation criteria | Score |
|---|---|---|
| Odor | Unpleasant odor is not sensed. Comfortable scent. | 0 point |
| | Unpleasant odor is slightly sensed. | 1 point |
| | Unpleasant odor is sensed. | 2 points |
| | Unpleasant odor is strongly sensed. | 3 points |
| | Strongly unpleasant odor is sensed very strongly. | 4 points |

Evaluation Results

TABLE 5

| Reaction conditions | Odor score |
|---|---|
| Example 2 (the extract) | 0.4 |
| Control (Non-extract) | 1.6 |

As the result, the extract of Example 2 had a less unpleasant odor than the control, and it was suggested that the extract had a flavor suitable for a drink.

Example 3

Sensory Evaluation for a Bitter Taste

A bitter taste was compared for the extract of Example 2 by sensory evaluation.

Evaluation Method in the Sensory Evaluation for a Bitter Taste

For a bitter taste of the extract of Example 2 and the product (the control) obtained by extracting an unoxidized hop pellet according to a similar method as Example 2, sensory evaluation was performed by a panel of six in-house staffs according to the following methods. The extract was boiled and dissolved in 10 mM citrate buffer (pH 5.5), and the extract of Example 2 or the control was diluted to give 50 ppm in terms of isohumulone equivalence, and used for the sensory evaluation.

Sensory evaluation was performed in which several mL of a sample was put into the mouth, and evaluated in accordance with the evaluation criteria. The result was calculated as the mean of scores from the six staffs.

Evaluation Criteria

TABLE 6

| Evaluation items | Evaluation criteria | Score |
|---|---|---|
| Bitter taste | Bitter taste is not sensed. | 0 point |
| | Bitter taste is slightly sensed. | 1 point |
| | Bitter taste is sensed. | 2 points |
| | Bitter taste is strongly sensed. | 3 points |
| | Bitter taste is sensed too strongly to drink. | 4 points |

Evaluation Results

TABLE 7

| Reaction conditions | Bitter taste score |
|---|---|
| Control | 3.4 |
| Example 2 | 1.2 |

As the result, the extract of Example 2 showed a reduced bitter taste, and it was suggested that the extract had a flavor suitable for a drink.

Example 4

Studies of the Temperature and Time for the Oxidation-Reaction

In accordance with the method of Example 1, a hop pellet was oxidized at 60° C. or 80° C., and the product was sampled over time to be measured by HPLC. The peak area ratio 1 of the total peak area of the peak area of α acid, β acid and iso α acid to the area of all the peaks, and the peak area ratio 2 of the peak area other than humulones, lupulones and isohumulones to the area of all the peaks were computed. Sensory evaluation was also performed in accordance with the method described in Example 3. The results were as follows.

TABLE 8

| Heating temperature (° C.) | Heating time (hour) | Peak area ratio 1 (%) | Peak area ratio 2 (%) | Bitter taste score |
|---|---|---|---|---|
| Unheated | — | 88.9 | 11.1 | 3.4 |
| 60° C. | 32 | 26.0 | 74.0 | 1.7 |
| 60° C. | 48 | 12.7 | 87.3 | 1.1 |
| 60° C. | 120 | 8.0 | 92.0 | 1.1 |
| 80° C. | 4 | 25.1 | 74.9 | 2.1 |
| 80° C. | 8 | 10.7 | 89.3 | 0.7 |
| 80° C. | 24 | 3.0 | 97.0 | 1.2 |

The results revealed that the bitter taste scores were nearly correlated with the peak area ratios, and proportional to the reaction temperature/time, i.e., when the heating temperature increased, the time required for the peak area ratio 2 to reach 80% or more (the peak area ratio 1 is 20% or less) can be shortened, and the bitter taste can be efficiently reduced.

Example 5

Studies of the Oxidation Treatment at Low Temperature

In accordance with the method of Example 1, the hop of Sarz variety was kept at 4° C. for five years, and the oxidation treatment was performed.

The resulting product was subjected to HPLC analysis.

Figure 3:
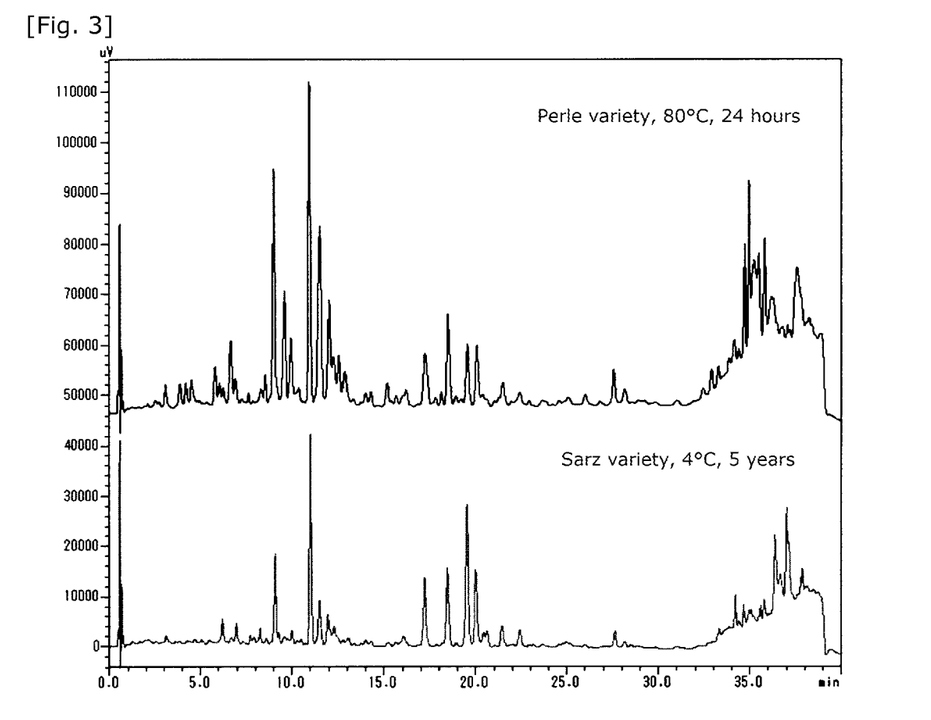
FIG. 3 is a HPLC chart of a product obtained by oxidization at low temperature (Example 5).

FIG. 3 shows a HPLC analysis chromatogram for the analysis of the product of Example 5. It was found that similar products can be obtained regardless of hop varieties and reaction temperatures.

Example 6

Preparation of a Sample for Evaluating a Physiological Activity

In order to evaluate a physiological activity of the product of the present invention, a sample was prepared by the following methods.

Figure 4:
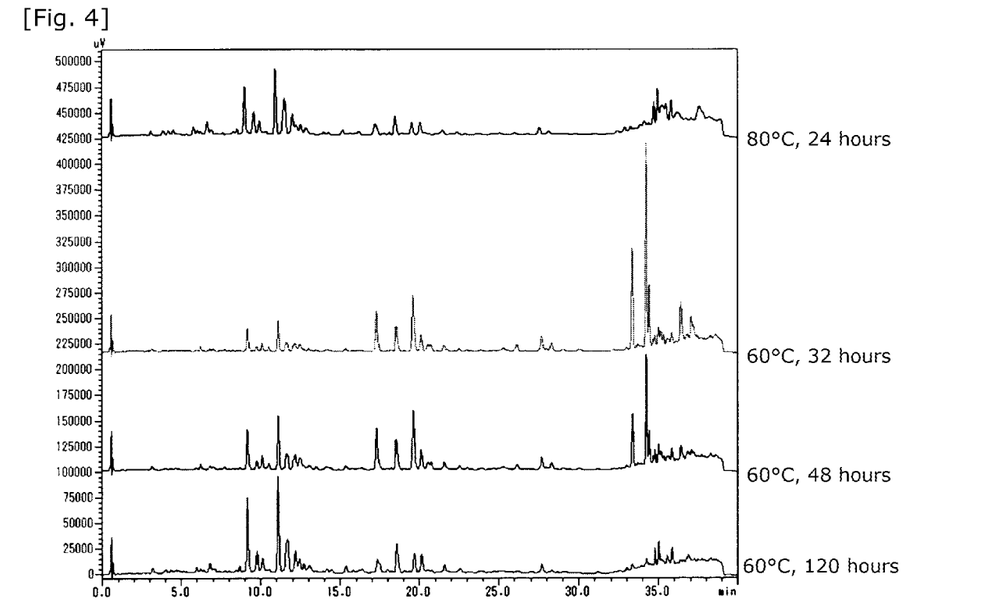
FIG. 4 shows a HPLC chart of an extract (Example 6) obtained by oxidizing a hop followed by ethanol-extraction, which was used for evaluating a physiological activity (Example 8).

In accordance with the method described in Examples 1 and 2, an extract was obtained by heat reacting a hop at 60° C. for 32 hours, 48 hours, 120 hours. The extract prepared in this way and the extract of Example 2 were applied for evaluating a physiological activity. Each extract was subjected to HPLC analysis after dilution to confirm that a hop oxidation-reaction product had been extracted (FIG. 4).

Example 7

Evaluation of an Effect on Fatty Acid Accumulation and the Like

For the extract of Example 2, physiological evaluation was performed with use of a mouse. Six 5-week old male C57BL/6J mice (Charles River Laboratories Japan Inc.) per group were habituated with a feed of AIN93G for about 1 week, and then a total of two groups were prepared: a high fat diet group and a group in which the extract of Example 2 was added to the high fat diet in a solid content of 0.5% (W/W). From the start of administration, body weight was measured every week, and administration was continued up to Day 37. When dissection, subcutaneous fat weight and perirenal fat weight were measured.

TABLE 9

| High fat diet composition | |
|---|---|
| | Mixing ratio (%) |
| Milk casein | 29.00 |
| L-cystine | 0.440 |
| Sucrose | 23.28 |
| Safflower oil | 33.50 |
| Cellulose powder | 7.250 |
| AIN93G mineral | 5.080 |
| AIN93G mineral (with choline) | 1.450 |

Figure 5:
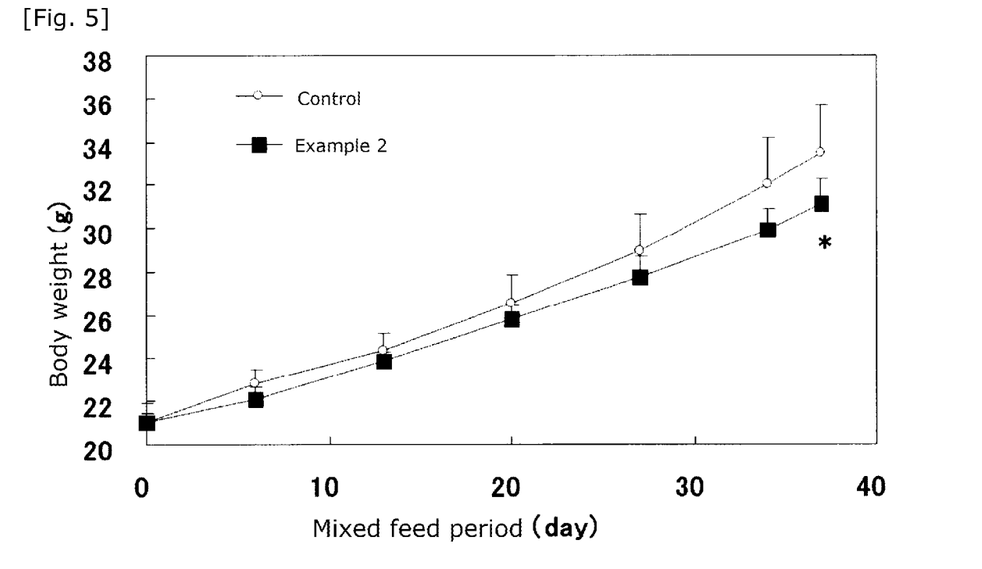
FIG. 5 shows an effect of the extract (Example 2) obtained by oxidizing a hop followed by ethanol-extraction on the change in body weight of a high dietary fat intake mouse.
Figure 6:
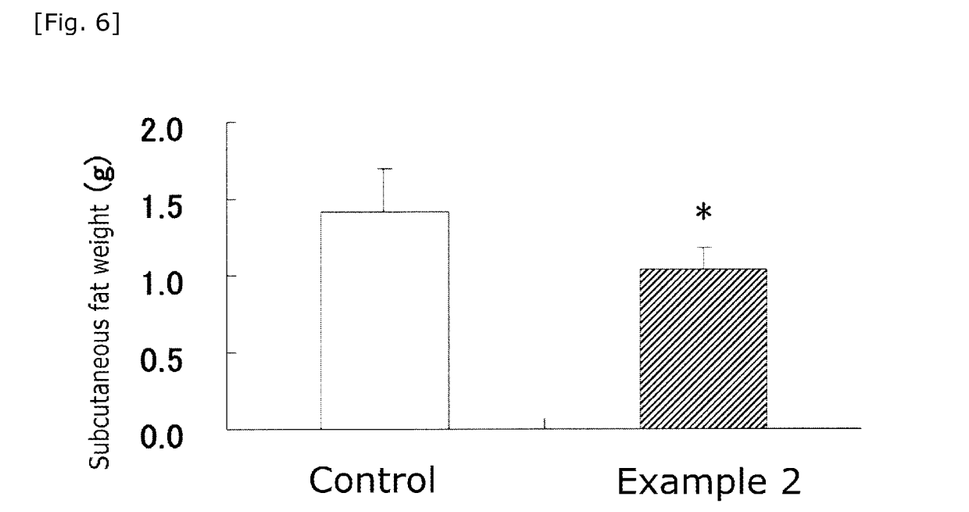
FIG. 6 shows an effect of the product obtained from the extract (Example 2) obtained by oxidizing a hop followed by ethanol-extraction on the change in weight of subcutaneous fat of a high dietary fat intake mouse.
Figure 7:
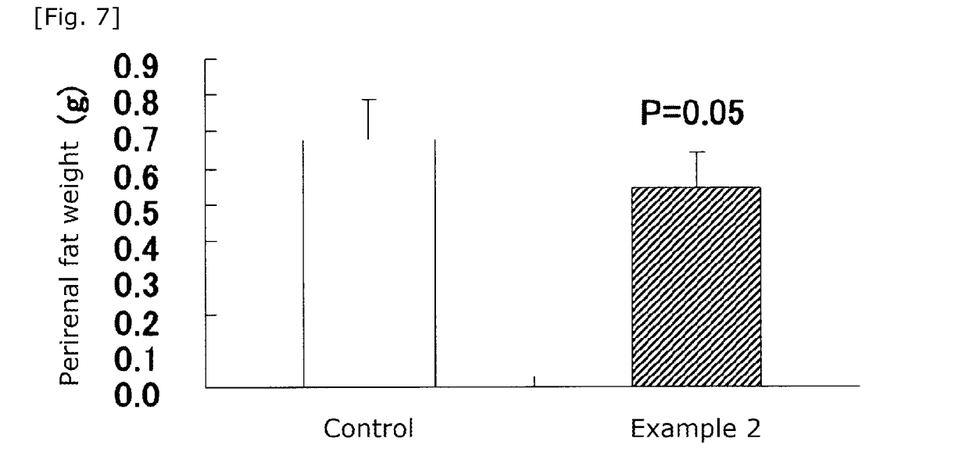
FIG. 7 shows an effect of the extract (Example 2) obtained by oxidizing a hop followed by ethanol-extraction on the change in weight of perirenal fat of a high dietary fat intake mouse.

The results showed that in the group where the 0.5% extract of Example 2 was added, a significant weight gain suppressing effect was observed as compared with the high fat diet group (FIG. 5: body weight; mean±standard deviation; *:P<0.05 (as compared with the control group)). A significant decrease in subcutaneous fat weight and a tendency of decrease in perirenal fat weight were also observed (FIG. 6 and FIG. 7: subcutaneous fat weight and perirenal fat weight respectively; mean±standard deviation; *:P<0.05 (as compared with the control group)). The results described above demonstrated that the hop oxidation-reaction product has a fat accumulation suppressing effect. In general, one possible mechanism of the fat accumulation suppressing effect is suppressed absorption of lipid in the test diet. Therefore, next, in order to evaluate a lipid absorption suppressing activity of the extract of Example 2, an inhibitory effect of the pancreatic lipase activity which contributes largely to absorption of neutral fat was evaluated.

Example 8

Evaluation of a Pancreatic Lipase Activity Inhibitory Effect of the Hop Oxidation-Reaction Product A pancreatic lipase activity inhibitory effect of the extract of Example 2 was evaluated. Measurements of the pancreatic lipase activity was performed as follows in accordance with the reported method (J. Agric. Food Chem., 53, 4593-4598 (2005)). For a measurement reagent, 4-methylumbelliferyloleate (Sigma Aldrich) was used, and 10 U of swine pancreatic lipase (Sigma Aldrich) was used per sample as an enzyme source. The extract of Example 2 was dissolved by using 4% dimethyl sulfoxide to give a predetermined concentration of the solid content, and then subjected to the test.

Activities were expressed as the enzyme activity obtained when only 4% dimethyl sulfoxide was added to be 100%.

Figure 8:
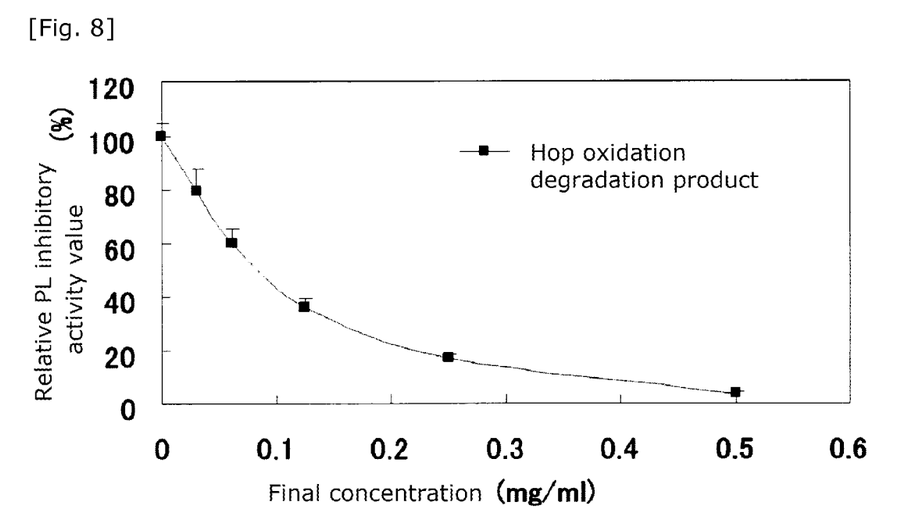
FIG. 8 shows a pancreatic lipase inhibitory activity of the extract (Example 2) obtained by oxidizing a hop followed by ethanol-extraction.

The results showed that the hop oxidation-reaction product inhibited the pancreatic lipase activity, and when added in a final concentration of 82.8 μg/ml, the lipase activity decreased down to about 50% (FIG. 8: the pancreatic lipase inhibitory effect of the hop oxidation-reaction product; mean±standard deviation). The results described above demonstrated that the extract of Example 2 has an inhibitory effect of the pancreatic lipase activity.

Next, the pancreatic lipase activity inhibitory effect was similarly evaluated for the extracts obtained in Example 6.

Figure 9:
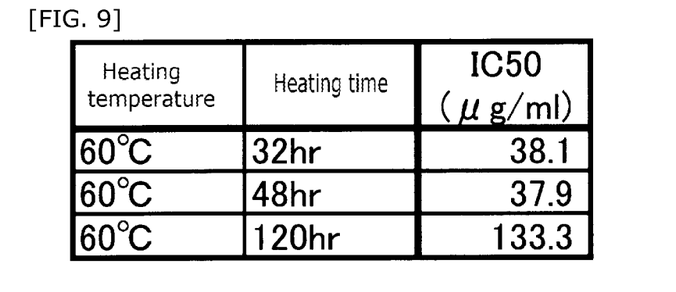
FIG. 9 shows 50% inhibitory concentrations for the pancreatic lipase activity (IC50) of the extracts obtained by oxidizing a hop followed by ethanol-extraction (Example 6).

The results from the measurements showed that all the extracts obtained in Example 6 inhibited the pancreatic lipase activity, and when added in a final concentration of the solid content of 37.9 to 133.3 μg/ml, the lipase activity decreased down to about 50%. Further, the 50% inhibitory concentrations for the pancreatic lipase activity (IC50) of the extracts obtained in Example 6 were as shown in FIG. 9. The results described above demonstrated that all the extracts obtained in Example 6 have a pancreatic lipase activity inhibitory effect.

The invention claimed is:

1. A hop oxidation-reaction product wherein a proportion of a peak area of iso α acid, α acid and β acid to a total peak area (mAU·min) of all the peaks of the hop oxidation-reaction product as determined by HPLC analysis is 20% or less and wherein a proportion of a peak area of the components other than α acid, β acid and iso α acid indicated by the arrow A shown in FIG. 1A to a total peak area (mAU·min) of all the peaks of the hop oxidation-reaction product as determined by HPLC analysis is 80% or more, wherein said HPLC is performed under the following conditions:

Column: C18 2.1 mm I.D.×100 mm, particle diameter: 3 μm
Flow rate: 0.6 mL/min
Elution solvent A: water/phosphoric acid, 1000/0.2 (v/v)+ EDTA (free) 0.02% (w/v)
Elution solvent B: acetonitrile
Elution solvent C: water
Injection amount: 3 μL
Column temperature: 40° C.
Detection wavelength: 270 nm (oxidation-reaction products, iso α acid, α acid, β acid)
Gradient program:

|  | Mobile phase composition % | | |
| --- | --- | --- | --- |
| Time min | A | B | C |
| 0 | 90 | 10 | 0 |
| 26.67 | 48 | 52 | 0 |
| 30 | 25 | 75 | 0 |
| 32.67 | 15 | 85 | 0 |
| 37.67 | 15 | 85 | 0 |
| 37.68 | 0 | 10 | 90 |
| 41.3 | 0 | 10 | 90 |
| 41.31 | 90 | 10 | 0 |
| 51 |  | stop |  |

(After 37.68 min, the washing and equilibration step)

and
wherein the hop oxidation-reaction product is obtained by heating a hop in air from 24 to 120 hours at a temperature of 65° C. to 80° C., and wherein the hop oxidation-reaction product suppresses lipid absorption or inhibits pancreatic lipase activity in mammals.

2. A hop-derived extract obtainable by extracting the hop oxidation-reaction product according to claim 1 with an aqueous solvent.

3. A food additive comprising the oxidation-reaction product according to claim 1 and an orally acceptable carrier.

4. A food product comprising the oxidation-reaction product according to claim 1 and an orally acceptable carrier.

5. A method of preparing the hop oxidation-reaction product according to claim 1, the method comprising subjecting a hop to an oxidation treatment, wherein the oxidation treatment is performed by heating the hop in air from 24 to 120 hours at a temperature of 65° C. to 80° C.

6. A method of preparing the hop-derived extract, comprising extracting the hop oxidation-reaction product according to claim 1 with an aqueous solvent.

7. The method according to claim 6, wherein the aqueous solvent is selected from the group consisting of water, alcohol, and a combination thereof.

8. A food additive comprising the hop-derived extract according to claim 2 and an orally acceptable carrier.

9. A food product comprising the hop-derived extract according to claim 2 and an orally acceptable carrier.

10. The hop-derived extract according to claim 2, wherein the aqueous solvent is selected from the group consisting of water, alcohol, and a combination thereof.

11. The hop oxidation-reaction product according to claim 1, wherein the proportion of a peak area of iso a acid, α acid and β acid to a total peak area (mAU·min) of all the peaks of the hop oxidation-reaction product as determined by HPLC analysis is 10% or less, and wherein the proportion of a peak area of the components other than α acid, β acid and iso α acid indicated by the arrow A shown in FIG. 1A to a total peak area (mAU·min) of all the peaks of the hop oxidation-reaction product as determined by HPLC analysis is 90% or more.

12. An oral preparation comprising the hop oxidation-reaction product according to claim 1 and, gelatin or dextrin.

13. The oral preparation according to claim 12, which is a tablet or a capsule.

14. The food product according to claim 4, which is a non-alcohol beer having 1% or less alcohol content.

* * * * *

UNITED STATES PATENT AND TRADEMARK OFFICE
CERTIFICATE OF CORRECTION

| | |
|---|---|
| PATENT NO. | : 11,179,429 B2 |
| APPLICATION NO. | : 13/994624 |
| DATED | : November 23, 2021 |
| INVENTOR(S) | : Manabe et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 704 days.

Signed and Sealed this
Twentieth Day of December, 2022

*Katherine Kelly Vidal*

Katherine Kelly Vidal
*Director of the United States Patent and Trademark Office*